United States Patent
Rotem et al.

(10) Patent No.: US 9,657,902 B2
(45) Date of Patent: May 23, 2017

(54) PERISTALTIC INFUSION PUMP WITH LOCKING MECHANISM

(71) Applicant: Q-CORE MEDICAL LTD., Petach Tikva (IL)

(72) Inventors: Shachar Rotem, Kibbutz Metzer (IL); Ori Goldor, Amikam (IL)

(73) Assignee: Q-CORE MEDICAL LTD., Petach Tikva (IL)

( * ) Notice: Subject to any disclaimer, the term of this patent is extended or adjusted under 35 U.S.C. 154(b) by 4 days.

(21) Appl. No.: 13/651,420

(22) Filed: Oct. 14, 2012

(65) Prior Publication Data

US 2013/0116623 A1 May 9, 2013

Related U.S. Application Data

(63) Continuation of application No. 12/464,202, filed on May 12, 2009, now Pat. No. 8,308,457, which is a (Continued)

(30) Foreign Application Priority Data

Nov. 24, 2004 (IL) .......................... 165365
Nov. 13, 2006 (IL) .......................... 179228

(51) Int. Cl.
*F04B 43/12* (2006.01)
*F17D 3/00* (2006.01)
(Continued)

(52) U.S. Cl.
CPC ........... *F17D 3/00* (2013.01); *A61M 5/14228* (2013.01); *A61M 5/16813* (2013.01);
(Continued)

(58) Field of Classification Search
CPC .............. A61M 5/142; A61M 5/14228; A61M 2205/12; A61M 2205/14; F04B 43/12; F04B 43/082
(Continued)

(56) References Cited

U.S. PATENT DOCUMENTS 2,056,322 A 10/1936 Hoppe
2,393,838 A 1/1946 Tarbox
(Continued)

FOREIGN PATENT DOCUMENTS

DE 10118086 A1 7/2002
EP 0215249 A1 3/1987
(Continued)

OTHER PUBLICATIONS

Honeywell Sensing and Control, "FSSI500NSB force sensor", Golden Valley, Minnesota, USA, 1998-2004 http://sccatalog.honeywell.com/imc/printfriendly.asp?FAM~force&PN~FSSI500NSB (5 pages).
(Continued)

*Primary Examiner* — Patrick Hamo
(74) *Attorney, Agent, or Firm* — Vladimir Sherman; Professional Patent Solutions

(57) ABSTRACT

A medical device includes an interface unit body, which is configured to hold a portion of a flexible infusion tube. A hinge insert is fixed to the interface unit body and is configured to engage a hinge receptacle, which defines a hinge axis, on an infusion pump. A catch insert is fixed to the interface unit body and is configured to lock onto a catch receptacle on the infusion pump upon rotation of the mechanical interface unit about the hinge axis while the hinge insert engages the hinge receptacle, so as to bring the tube into engagement with a peristaltic mechanism of the infusion pump in order to enable the peristaltic mechanism to propel a fluid through the tube.

6 Claims, 6 Drawing Sheets

Related U.S. Application Data continuation-in-part of application No. 11/791,599, filed as application No. PCT/IL2005/001249 on Nov. 24, 2005, now Pat. No. 8,029,253, and application No. 12/464,202, which is a continuation-in-part of application No. PCT/IL2007/001399, filed on Nov. 13, 2007.

(51) Int. Cl.
| | |
|---|---|
| *A61M 5/142* | (2006.01) |
| *A61M 39/28* | (2006.01) |
| *F04B 43/08* | (2006.01) |
| *A61M 5/168* | (2006.01) |

(52) U.S. Cl.
CPC ......... *A61M 39/281* (2013.01); *F04B 43/082* (2013.01); *F04B 43/12* (2013.01); *Y10T 137/0318* (2015.04); *Y10T 137/85978* (2015.04)

(58) Field of Classification Search
USPC ...... 417/474, 477.2, 478, 479; 604/151, 153
See application file for complete search history.

(56) References Cited

U.S. PATENT DOCUMENTS

| | | |
|---|---|---|
| 2,743,898 A | 5/1956 | King |
| 2,981,115 A | 4/1961 | Beguin |
| 3,443,585 A | 5/1969 | Reinicke |
| 3,511,583 A | 5/1970 | Brown |
| 3,677,667 A | 7/1972 | Morrison |
| 3,778,195 A | 12/1973 | Bamberg |
| 3,982,722 A | 9/1976 | Bernard |
| 3,982,725 A | 9/1976 | Clark |
| 4,014,318 A | 3/1977 | Dockum et al. |
| 4,039,269 A | 8/1977 | Pickering |
| 4,155,362 A | 5/1979 | Jess |
| 4,178,138 A | 12/1979 | Iles |
| 4,236,880 A | 12/1980 | Archibald |
| 4,270,532 A | 6/1981 | Franetzki et al. |
| 4,290,346 A | 9/1981 | Bujan |
| 4,320,781 A | 3/1982 | Bouvet et al. |
| 4,373,525 A | 2/1983 | Kobayashi |
| 4,450,375 A | 5/1984 | Siegal |
| 4,479,797 A | 10/1984 | Kobayashi et al. |
| 4,489,863 A | 12/1984 | Horchos et al. |
| 4,493,706 A | 1/1985 | Borsanyi et al. |
| 4,650,469 A | 3/1987 | Berg et al. |
| 4,671,792 A | 6/1987 | Borsanyi |
| 4,682,135 A | 7/1987 | Yamakawa |
| 4,690,673 A | 9/1987 | Bloomquist |
| 4,725,205 A | 2/1988 | Cannon et al. |
| 4,728,265 A | 3/1988 | Cannon |
| 4,741,736 A | 5/1988 | Brown |
| 4,748,003 A | 5/1988 | Riley |
| 4,755,168 A | 7/1988 | Romanelli et al. |
| 4,836,752 A | 6/1989 | Burkett |
| 4,867,744 A | 9/1989 | Borsanyi |
| 4,893,991 A | 1/1990 | Heminway et al. |
| 4,927,411 A | 5/1990 | Pastrone et al. |
| 4,954,046 A | 9/1990 | Irvin et al. |
| 4,954,256 A | 9/1990 | Degen et al. |
| 4,978,335 A | 12/1990 | Arthur, III |
| 5,074,756 A | 12/1991 | Davis |
| 5,078,683 A | 1/1992 | Sancoff et al. |
| 5,088,904 A | 2/1992 | Okada |
| 5,096,385 A | 3/1992 | Georgi et al. |
| 5,103,211 A | 4/1992 | Daoud et al. |
| 5,151,019 A | 9/1992 | Danby et al. |
| 5,152,680 A | 10/1992 | Okada |
| 5,165,874 A | 11/1992 | Sancoff et al. |
| 5,213,483 A | 5/1993 | Flaherty et al. |
| 5,219,327 A | 6/1993 | Okada |
| 5,222,946 A | 6/1993 | Kamen |
| 5,246,347 A | 9/1993 | Davis |
| 5,257,978 A | 11/1993 | Haber et al. |
| 5,286,176 A | 2/1994 | Bonin |
| 5,290,158 A | 3/1994 | Okada |
| 5,308,333 A | 5/1994 | Skakoon |
| 5,338,157 A | 8/1994 | Blomquist |
| 5,395,320 A | 3/1995 | Padda et al. |
| 5,429,485 A | 7/1995 | Dodge |
| 5,485,408 A | 1/1996 | Blomquist |
| 5,499,969 A | 3/1996 | Beuchat et al. |
| 5,509,439 A | 4/1996 | Tantardini |
| 5,527,295 A | 6/1996 | Wing |
| 5,542,826 A | 8/1996 | Warner |
| 5,569,188 A | 10/1996 | Mackool |
| 5,575,309 A | 11/1996 | Connell |
| 5,575,631 A | 11/1996 | Jester |
| 5,577,891 A | 11/1996 | Loughnane et al. |
| 5,584,667 A | 12/1996 | Davis |
| 5,593,134 A | 1/1997 | Steber et al. |
| 5,601,420 A | 2/1997 | Warner et al. |
| 5,628,619 A | 5/1997 | Wilson |
| 5,658,250 A | 8/1997 | Blomquist et al. |
| 5,658,252 A | 8/1997 | Johnson |
| 5,660,529 A | 8/1997 | Hill |
| 5,669,877 A | 9/1997 | Blomquist |
| 5,683,233 A | 11/1997 | Moubayed et al. |
| 5,695,473 A | 12/1997 | Olsen |
| 5,704,584 A | 1/1998 | Winterer et al. |
| 5,742,519 A | 4/1998 | McClendon et al. |
| 5,782,805 A | 7/1998 | Meinzer et al. |
| 5,788,669 A | 8/1998 | Peterson |
| 5,791,880 A | 8/1998 | Wilson |
| 5,791,881 A | 8/1998 | Moubayed et al. |
| 5,803,712 A | 9/1998 | Davis et al. |
| 5,807,322 A | 9/1998 | Lindsey et al. |
| 5,810,323 A | 9/1998 | Winterer et al. |
| 5,853,386 A | 12/1998 | Davis et al. |
| 5,876,370 A | 3/1999 | Blomquist |
| 5,888,052 A | 3/1999 | Hill |
| 5,896,076 A | 4/1999 | Van Namen |
| 5,909,724 A | 6/1999 | Nishimura et al. |
| 5,924,852 A | 7/1999 | Moubayed et al. |
| 5,935,099 A | 8/1999 | Peterson et al. |
| 5,935,106 A | 8/1999 | Olsen |
| 5,943,633 A | 8/1999 | Wilson et al. |
| 5,954,485 A | 9/1999 | Johnson et al. |
| 5,980,490 A | 11/1999 | Tsoukalis |
| 5,996,964 A | 12/1999 | Ben-Shalom |
| 6,024,539 A | 2/2000 | Blomquist |
| 6,095,189 A | 8/2000 | Ben-Shalom |
| 6,110,153 A | 8/2000 | Davis et al. |
| 6,146,109 A | 11/2000 | Davis et al. |
| 6,164,921 A | 12/2000 | Moubayed et al. |
| 6,165,874 A | 12/2000 | Powell et al. |
| RE37,074 E | 2/2001 | Danby et al. |
| 6,203,296 B1 | 3/2001 | Ray et al. |
| 6,213,723 B1 | 4/2001 | Danby et al. |
| 6,213,739 B1 | 4/2001 | Phallen et al. |
| 6,234,773 B1 | 5/2001 | Hill et al. |
| 6,241,704 B1 | 6/2001 | Peterson et al. |
| 6,261,262 B1 | 7/2001 | Briggs et al. |
| 6,280,408 B1 | 8/2001 | Sipin |
| 6,312,227 B1 | 11/2001 | Davis |
| 6,339,410 B1 | 1/2002 | Milner et al. |
| 6,347,553 B1 | 2/2002 | Morris et al. |
| 6,371,732 B1 | 4/2002 | Moubayed et al. |
| 6,422,057 B1 | 7/2002 | Anderson |
| 6,450,773 B1 | 9/2002 | Upton |
| 6,475,180 B2 | 11/2002 | Peterson et al. |
| 6,519,569 B1 | 2/2003 | White et al. |
| 6,537,244 B2 | 3/2003 | Paukovits et al. |
| 6,544,171 B2 | 4/2003 | Beetz et al. |
| 6,558,347 B1 | 5/2003 | Jhuboo et al. |
| 6,572,604 B1 | 6/2003 | Platt et al. |
| 6,622,542 B2 | 9/2003 | Derek et al. |
| 6,648,861 B2 | 11/2003 | Platt et al. |
| 6,692,241 B2 | 2/2004 | Watanabe et al. |
| 6,733,476 B2 | 5/2004 | Christenson et al. |
| 6,742,992 B2 | 6/2004 | Davis |

(56) References Cited

U.S. PATENT DOCUMENTS

| | | |
|---|---|---|
| 6,749,587 B2 | 6/2004 | Flaherty |
| 6,768,425 B2 | 7/2004 | Flaherty et al. |
| 6,788,199 B2 | 9/2004 | Crabtree et al. |
| 6,790,198 B1 | 9/2004 | White et al. |
| 6,902,549 B2 | 6/2005 | Marmaropoulos et al. |
| 6,942,473 B2 | 9/2005 | Abrahamson et al. |
| 7,018,361 B2 | 3/2006 | Gillespie, Jr. et al. |
| 7,022,075 B2 | 4/2006 | Grunwald et al. |
| 7,048,720 B1 | 5/2006 | Thorne, Jr. et al. |
| 7,059,840 B2 | 6/2006 | Corwin et al. |
| 7,122,026 B2 | 10/2006 | Rogers et al. |
| 7,131,966 B1 | 11/2006 | Tamari |
| 7,163,385 B2 | 1/2007 | Gharib et al. |
| 7,347,836 B2 | 3/2008 | Peterson et al. |
| 7,525,432 B2 | 4/2009 | Jackson |
| 7,556,481 B2 | 7/2009 | Moubayed |
| 7,645,258 B2 | 1/2010 | White et al. |
| 7,654,976 B2 | 2/2010 | Peterson et al. |
| 7,695,255 B2 | 4/2010 | Ben-Shalom et al. |
| 7,698,156 B2 | 4/2010 | Martucci et al. |
| 7,704,227 B2 | 4/2010 | Moberg et al. |
| 7,762,795 B2 | 7/2010 | Moubayed |
| 7,840,260 B2 | 11/2010 | Epley |
| 7,892,332 B2 | 2/2011 | Prisco et al. |
| 7,896,834 B2 | 3/2011 | Smisson, III et al. |
| 7,935,102 B2 | 5/2011 | Breznock et al. |
| 7,938,796 B2 | 5/2011 | Moubayed et al. |
| 7,963,946 B2 | 6/2011 | Moubayed et al. |
| 7,998,121 B2 | 8/2011 | Stringham |
| 8,025,634 B1 | 9/2011 | Moubayed et al. |
| 8,029,253 B2 | 10/2011 | Rotem et al. |
| 8,142,400 B2 | 3/2012 | Rotem et al. |
| 8,182,445 B2 | 5/2012 | Moubayed et al. |
| 8,197,235 B2 | 6/2012 | Davis |
| 8,214,231 B2 | 7/2012 | Martucci et al. |
| 8,234,128 B2 | 7/2012 | Martucci et al. |
| 8,241,018 B2 | 8/2012 | Harr |
| 8,257,654 B2 | 9/2012 | Maus et al. |
| 8,308,457 B2 | 11/2012 | Rotem et al. |
| 8,334,768 B2 | 12/2012 | Eaton et al. |
| 8,337,168 B2 | 12/2012 | Rotem et al. |
| 8,343,111 B2 | 1/2013 | Beck et al. |
| 8,352,290 B2 | 1/2013 | Bartz et al. |
| 8,363,583 B2 | 1/2013 | Jia et al. |
| 8,371,832 B2 | 2/2013 | Rotem et al. |
| 8,444,587 B2 | 5/2013 | Kelly et al. |
| 8,489,427 B2 | 7/2013 | Simpson et al. |
| 8,535,025 B2 | 9/2013 | Rotem et al. |
| 8,579,816 B2 | 11/2013 | Kamath et al. |
| 8,666,367 B2 | 3/2014 | Sharp et al. |
| 8,672,875 B2 | 3/2014 | Vanderveen et al. |
| 8,678,793 B2 | 3/2014 | Goldor et al. |
| 8,920,144 B2 | 12/2014 | Rotem et al. |
| 9,056,160 B2 | 6/2015 | Rotem et al. |
| 2001/0029321 A1 | 10/2001 | Beetz et al. |
| 2002/0056675 A1 | 5/2002 | Hegde |
| 2002/0094287 A1 | 7/2002 | Davis |
| 2002/0156402 A1 | 10/2002 | Woog et al. |
| 2002/0165503 A1 | 11/2002 | Morris et al. |
| 2003/0034887 A1 | 2/2003 | Crabtree et al. |
| 2003/0040700 A1 | 2/2003 | Hickle et al. |
| 2003/0065536 A1 | 4/2003 | Hansen et al. |
| 2003/0109988 A1 | 6/2003 | Geissler et al. |
| 2003/0140928 A1 | 7/2003 | Bui et al. |
| 2003/0141981 A1 | 7/2003 | Bui et al. |
| 2003/0182586 A1 | 9/2003 | Numano |
| 2004/0167804 A1 | 8/2004 | Simpson et al. |
| 2004/0172222 A1 | 9/2004 | Simpson et al. |
| 2004/0181314 A1 | 9/2004 | Zaleski |
| 2004/0191112 A1 | 9/2004 | Hill et al. |
| 2004/0204673 A1 | 10/2004 | Flaherty |
| 2004/0204685 A1 | 10/2004 | Wright et al. |
| 2004/0235446 A1 | 11/2004 | Flaherty et al. |
| 2005/0001369 A1 | 1/2005 | Cross |
| 2005/0022274 A1 | 1/2005 | Campbell et al. |
| 2005/0055242 A1 | 3/2005 | Bello et al. |
| 2005/0088409 A1 | 4/2005 | Van Berkel |
| 2005/0112001 A1 | 5/2005 | Bahnen et al. |
| 2005/0171501 A1 | 8/2005 | Kelly |
| 2005/0191196 A1 | 9/2005 | Tanner et al. |
| 2005/0214146 A1 | 9/2005 | Corwin et al. |
| 2006/0051218 A1 | 3/2006 | Harttig |
| 2006/0083644 A1 | 4/2006 | Zumbrum et al. |
| 2006/0173419 A1 | 8/2006 | Malcolm |
| 2006/0213249 A1 | 9/2006 | Uram et al. |
| 2007/0032098 A1 | 2/2007 | Bowles et al. |
| 2007/0048161 A1 | 3/2007 | Moubayed |
| 2007/0060872 A1 | 3/2007 | Hall et al. |
| 2007/0118405 A1 | 5/2007 | Campbell et al. |
| 2007/0135866 A1 | 6/2007 | Baker et al. |
| 2007/0154336 A1 | 7/2007 | Miyazaki et al. |
| 2007/0217931 A1 | 9/2007 | Estes et al. |
| 2007/0269324 A1 | 11/2007 | Goldor et al. |
| 2008/0015506 A1 | 1/2008 | Davis |
| 2008/0065007 A1 | 3/2008 | Peterson et al. |
| 2008/0065016 A1 | 3/2008 | Peterson et al. |
| 2008/0067462 A1 | 3/2008 | Miller et al. |
| 2008/0071251 A1 | 3/2008 | Moubayed et al. |
| 2008/0095649 A1 | 4/2008 | Ben-Shalom et al. |
| 2008/0144560 A1 | 6/2008 | Jia et al. |
| 2008/0145249 A1 | 6/2008 | Smisson et al. |
| 2008/0146995 A1 | 6/2008 | Smisson et al. |
| 2008/0275307 A1 | 11/2008 | Poschmann |
| 2009/0088675 A1 | 4/2009 | Kelly et al. |
| 2009/0163864 A1 | 6/2009 | Breznock et al. |
| 2009/0203329 A1 | 8/2009 | White et al. |
| 2009/0221964 A1 | 9/2009 | Rotem et al. |
| 2009/0240201 A1 | 9/2009 | Rotem et al. |
| 2009/0270810 A1 | 10/2009 | DeBelser et al. |
| 2009/0300507 A1 | 12/2009 | Raghavan et al. |
| 2009/0317268 A1 | 12/2009 | Rotem et al. |
| 2010/0016781 A1 | 1/2010 | Nakayama et al. |
| 2010/0036322 A1 | 2/2010 | Rotem |
| 2010/0082001 A1 | 4/2010 | Beck et al. |
| 2010/0168545 A1 | 7/2010 | Kamath et al. |
| 2010/0211002 A1 | 8/2010 | Davis |
| 2010/0228223 A1 | 9/2010 | Williams et al. |
| 2010/0234708 A1 | 9/2010 | Buck et al. |
| 2010/0279652 A1 | 11/2010 | Sharp et al. |
| 2011/0148624 A1 | 6/2011 | Eaton et al. |
| 2011/0152772 A1 | 6/2011 | Rotem et al. |
| 2011/0152831 A1 | 6/2011 | Rotem et al. |
| 2011/0167133 A1 | 7/2011 | Jain |
| 2011/0251856 A1 | 10/2011 | Maus et al. |
| 2011/0264043 A1 | 10/2011 | Kotnik et al. |
| 2011/0276000 A1 | 11/2011 | Stringham |
| 2011/0282291 A1 | 11/2011 | Ciccone |
| 2011/0318208 A1 | 12/2011 | Goldor et al. |
| 2012/0059389 A1 | 3/2012 | Larson et al. |
| 2012/0062387 A1 | 3/2012 | Vik et al. |
| 2012/0136305 A1 | 5/2012 | Gagliardoni et al. |
| 2012/0241525 A1 | 9/2012 | Borges et al. |
| 2013/0006666 A1 | 1/2013 | Schneider et al. |
| 2013/0046508 A1 | 2/2013 | Sur et al. |
| 2013/0116620 A1 | 5/2013 | Rotem et al. |
| 2013/0116623 A1 | 5/2013 | Rotem et al. |
| 2013/0142670 A1 | 6/2013 | Rotem et al. |
| 2013/0209275 A1 | 8/2013 | Rotem et al. |
| 2013/0279370 A1 | 10/2013 | Eitan et al. |
| 2013/0345623 A1 | 12/2013 | Kopperschmidt et al. |
| 2014/0005631 A1 | 1/2014 | Rotem et al. |
| 2014/0119954 A1 | 5/2014 | Schweitzer et al. |
| 2014/0197824 A1 | 7/2014 | Gillespie et al. |
| 2014/0222377 A1 | 8/2014 | Bitan et al. |
| 2014/0276564 A1 | 9/2014 | Schneider |
| 2014/0369872 A1 | 12/2014 | Goldor et al. |
| 2014/0378901 A1 | 12/2014 | Rotem et al. |
| 2015/0038187 A1 | 2/2015 | Ho et al. |
| 2015/0073338 A1 | 3/2015 | Waldhoff et al. |
| 2015/0105726 A1 | 4/2015 | Qi et al. |
| 2015/0137988 A1 | 5/2015 | Gravenstein et al. |
| 2015/0141955 A1 | 5/2015 | Ruchti et al. |

(56) References Cited

U.S. PATENT DOCUMENTS

| | | |
|---|---|---|
| 2015/0172921 A1 | 6/2015 | Wang et al. |
| 2015/0182694 A1 | 7/2015 | Rosinko |
| 2015/0192120 A1 | 7/2015 | Rotem et al. |

FOREIGN PATENT DOCUMENTS

| | | |
|---|---|---|
| EP | 0225158 A2 | 6/1987 |
| EP | 0315312 A1 | 5/1989 |
| EP | 0429866 A1 | 6/1991 |
| EP | 0483794 A1 | 5/1992 |
| EP | 0858812 A2 | 8/1998 |
| EP | 1031358 A1 | 8/2000 |
| EP | 1350955 A2 | 10/2003 |
| EP | 1557186 | 7/2005 |
| EP | 1611834 A2 | 1/2006 |
| EP | 1485149 B1 | 7/2008 |
| FR | 2632529 A1 | 12/1989 |
| FR | 2753236 A1 | 3/1998 |
| JP | 60043188 A | 3/1985 |
| JP | 6-169992 A | 6/1994 |
| JP | 2002-57738 A | 2/2002 |
| JP | 2004141418 A | 5/2004 |
| WO | 8400691 A1 | 3/1984 |
| WO | 9116933 A1 | 11/1991 |
| WO | 9325816 A1 | 12/1993 |
| WO | 9408647 A1 | 4/1994 |
| WO | 9603168 A1 | 2/1996 |
| WO | 9630679 A1 | 10/1996 |
| WO | 9734084 A1 | 9/1997 |
| WO | 9804301 A1 | 2/1998 |
| WO | 9813080 A2 | 4/1998 |
| WO | 9847551 A1 | 10/1998 |
| WO | 99/58178 A1 | 11/1999 |
| WO | 0139816 A2 | 6/2001 |
| WO | 0165232 A1 | 9/2001 |
| WO | 0236044 A2 | 5/2002 |
| WO | 0238204 A2 | 5/2002 |
| WO | 0249509 A2 | 6/2002 |
| WO | 02068015 A2 | 9/2002 |
| WO | 03027503 A1 | 4/2003 |
| WO | 03080158 A1 | 10/2003 |
| WO | 2004070548 A2 | 8/2004 |
| WO | 2004093648 A2 | 11/2004 |
| WO | 2005089263 A2 | 9/2005 |
| WO | 2006/056986 A1 | 6/2006 |
| WO | 2007133259 A1 | 11/2007 |
| WO | 2008036658 A2 | 3/2008 |
| WO | 2008059492 A2 | 5/2008 |
| WO | 2008059493 A2 | 5/2008 |
| WO | 2008059494 A2 | 5/2008 |
| WO | 2008059495 A2 | 5/2008 |
| WO | 2008059496 A2 | 5/2008 |
| WO | 2008059498 A2 | 5/2008 |
| WO | 2008059499 A2 | 5/2008 |
| WO | 2008130644 A1 | 10/2008 |
| WO | 2010053702 A1 | 5/2010 |
| WO | 2010053703 A1 | 5/2010 |
| WO | 2010091313 A2 | 8/2010 |
| WO | 2011128850 A2 | 10/2011 |
| WO | 2012095827 A1 | 7/2012 |
| WO | 2012095829 A2 | 7/2012 |
| WO | 2013001425 A2 | 1/2013 |
| WO | 2013/028704 A1 | 2/2013 |
| WO | 2013/090748 A1 | 6/2013 |

OTHER PUBLICATIONS

International Application PCT/IL2007/001398 Search Report dated Jun. 11, 2008 (2 pages).
International Application PCT/IL2007/001398 Patentability Report dated May 19, 2009 (6 pages).
International Application PCT/IL2007/001399 Search Report dated Jun. 4, 2008 (3 pages).
International Application PCT/IL2007/001399 Patentability Report dated May 19, 2009 (9 pages).
International Application PCT/IL2007/001400 Search Report dated Jul. 15, 2008 (3 pages).
International Application PCT/IL2007/001400 Patentability Report dated May 19, 2009 (10 pages).
International Application PCT/IL2007/001401 Search Report dated Sep. 24, 2008 (2 pages).
International Application PCT/IL2007/001401 Patentability Report dated May 19, 2009 (11 pages).
International Application PCT/IL2007/001402 Search Report dated Jun. 20, 2008 (3 pages).
International Application PCT/IL2007/001402 Patentability Report dated May 19, 2009 (4 pages).
International Application PCT/IL2007/001404 Search Report dated Jul. 14, 2008 (2 pages).
International Application PCT/IL2007/001404 Patentability Report dated May 19, 2009 (7 pages).
International Application PCT/IL2007/001405 Search Report dated Jul. 21, 2008 (4 pages).
International Application PCT/IL2007/001405 Patentability Report dated May 19, 2009 (7 pages).
International Application PCT/IL2005/001249 Search Report dated Apr. 5, 2006 (18 pages).
International Application PCT/IL1997/000289 Search report dated Jan. 27, 1998 (18 pages).
International Application PCT/IL1997/000290 Search Report dated Jan. 27, 1998 (18 pages).
International Application PCT/IL2003/000947 Search Report dated Mar. 3, 2004 (43 pages).
International Application PCT/IB2011/051586 Search Report dated Oct. 27, 2011 (3 pages).
International Application PCT/IB2011/051586 Patentability Report dated Oct. 16, 2012 (9 pages).
International Application PCT/IB2012/050192 Search Report dated Aug. 17, 2012 (2 pages).
International Application PCT/IB2012/050192 Patentability Report dated Jul. 16, 2013 (6 pages).
International Application PCT/IB2012/050189 Search Report dated May 30, 2012 (2 pages).
International Application PCT/IB2012/050189 Patentability Report dated Jul. 16, 2013 (5 pages).
International Application PCT/IB2012/053149 Search Report dated Jan. 15, 2013 (2 pages).
U.S. Appl. No. 09/125,438 Official Action dated May 3, 1999 (4 pages).
U.S. Appl. No. 09/125,438 Official Action dated Jul. 15, 1999 (7 pages).
U.S. Appl. No. 10/535,103 Official Action dated Feb. 2, 2009 (9 pages).
European Application No. 05810500.8 Official Action dated Jul. 6, 2009 (5 pages).
European Application No. 05810500.8 Response to Official Action dated Jul. 6, 2009, submitted Oct. 15, 2009 (8 pages).
European Application No. 05810500.8 Official Action dated Jan. 23, 2012 (4 pages).
European Application No. 05810500.8 Response to Official Action dated Jan. 23, 2012, submitted May 22, 2012 (6 pages).
U.S. Appl. No. 11/791,599 Official Action (Non-Final) dated Aug. 19, 2010 (16 pages).
U.S. Appl. No. 11/791,599 Response to Official Action (Non-Final) dated Aug. 19, 2010, submitted Jan. 11, 2011 (8 pages).
U.S. Appl. No. 11/791,599 Official Action (Final) dated Mar. 31, 2011 (13 pages).
U.S. Appl. No. 11/791,599 Response to Official Action (Final) dated Mar. 31, 2011, submitted May 23, 2011 (7 pages).
U.S. Appl. No. 11/791,599 Notice of Allowance issued Jun. 14, 2011 (5 pages).
U.S. Appl. No. 13/229,798 Official Action (Non-Final) dated Dec. 26, 2012 (10 pages).
U.S. Appl. No. 13/229,798 Response to Official Action (Non-Final) dated Dec. 26, 2012, submitted Mar. 21, 2013 (13 pages).

(56) References Cited

OTHER PUBLICATIONS

U.S. Appl. No. 13/229,798 Notice of Allowance issued Apr. 19, 2013 (6 pages).
U.S. Appl. No. 13/229,798 Notice of Withdrawal from Issue dated May 13, 2013 (1 page).
U.S. Appl. No. 13/229,798 Official Action (Non-Final) dated Jun. 21, 2013 (6 pages).
Chinese Patent Application No. 200580045471.3 "Finger-type peristaltic pump" Official Action dated Jul. 18, 2008 and English translation thereof (7 pages).
Chinese Patent Application No. 200780041966.8 Official Action dated Jul. 13, 2010 (7 pages).
Chinese Patent Application No. 200780041966.8 Response to Official Action dated Jul. 13, 2010, as submitted (6 pages).
Chinese Patent Application No. 200780041966.8, translation of Notification of Grant, issued Jan. 28, 2011 (2 pages).
U.S. Appl. No. 12/464,202 Official Action (Non-Final) dated Oct. 3, 2011 (7 pages).
U.S. Appl. No. 12/464,202 Response to Official Action (Non-Final) dated Oct. 3, 2011, submitted Feb. 12, 2012 (12 pages).
U.S. Appl. No. 12/464,202 Notice of Allowance issued Jul. 11, 2012 (5 pages).
U.S. Appl. No. 12/463,399 Official Action (Non-Final) dated Jul. 21, 2011 (15 pages).
U.S. Appl. No. 12/463,399 Response to Official Action (Non-Final) dated Jul. 21, 2011, submitted Oct. 21, 2011 (5 pages).
U.S. Appl. No. 12/463,399 Official Action (Final) dated Dec. 13, 2011 (7 pages).
U.S. Appl. No. 12/463,399 Response to Official Action (Final) dated Dec. 13, 2011, submitted Feb. 12, 2012 (10 pages).
U.S. Appl. No. 12/463,399 Advisory Action and Applicant Initiated Interview Summary dated Mar. 8, 2012 (8 pages).
U.S. Appl. No. 12/463,399 Response to Official Action (Final) dated Dec. 13, 2011, submitted Mar. 26, 2012 with Request for Continued Examination (13 pages).
U.S. Appl. No. 12/463,399 Notice of Allowance issued Apr. 29, 2013 (14 pages).
U.S. Appl. No. 12/514,310 Official Action (Non-Final) dated Jul. 21, 2011 (8 pages).
U.S. Appl. No. 12/514,310 Response to Official Action (Non-Final) dated Jul. 21, 2011, submitted Oct. 21, 2011 (8 pages).
U.S. Appl. No. 12/514,310 Official Action (Final) dated Jan. 20, 2012 (10 pages).
U.S. Appl. No. 12/514,310 Response to Official Action (Final) dated Jan. 20, 2012, submitted Apr. 25, 2012 with Request for Continued Examination (11 pages).
U.S. Appl. No. 12/514,310 Official Action (Non-Final) dated May 25, 2012 (7 pages).
U.S. Appl. No. 12/514,310 Response to Official Action (Non-Final) dated May 25, 2012, submitted Jun. 28, 2012 (6 pages).
U.S. Appl. No. 12/514,310 Notice of Allowance issued Aug. 22, 2012 (7 pages).
U.S. Appl. No. 12/514,311 Official Action (Non-Final) dated Sep. 16, 2010 (10 pages).
U.S. Appl. No. 12/514,311 Response to Official Action (Non-Final) dated Sep. 16, 2010, submitted Dec. 9, 2010 (23 pages).
U.S. Appl. No. 12/514,311 Official Action (Final) dated Feb. 18, 2011 (7 pages).
U.S. Appl. No. 12/514,311 Examiner Interview Summary Record dated Mar. 4, 2011 (4 pages).
U.S. Appl. No. 12/514,311 Response to Official Action (Final) dated Feb. 18, 2011, submitted Mar. 31, 2011 with Request for Continued Examination (9 pages).
European Patent Application No. 10192477.7 Search Report dated May 10, 2011 (5 pages).
European Patent Application No. 10192477.7 Response to Search Report dated May 10, 2011, submitted Dec. 28, 2011.
U.S. Appl. No. 12/644,026 Official Action (Non-Final) dated Apr. 6, 2012 (12 pages).
U.S. Appl. No. 12/644,026 Response to Official Action (Non-Final) dated Apr. 6, 2012, submitted Jul. 5, 2012 (11 pages).
U.S. Appl. No. 12/644,026 Notice of Allowance issued Oct. 11, 2012 (10 pages).
U.S. Appl. No. 13/742,454 Official Action (Non-Final) dated Oct. 7, 2013 (13 pages).
U.S. Appl. No. 12/644,027 Official Action (Non-Final) dated Apr. 28, 2011 (7 pages).
U.S. Appl. No. 12/644,027 Response to Official Action (Non-Final) dated Apr. 28, 2011, submitted Jul. 21, 2011 (10 pages).
U.S. Appl. No. 12/644,027 Notice of Allowance issued Nov. 17, 2011 (5 pages).
U.S. Appl. No. 13/229,798 Response to Official Action (Non-Final) dated Jun. 21, 2013, submitted Oct. 21, 2013 (3 pages).
U.S. Appl. No. 13/229,798 Notice of Allowance issued Nov. 14, 2013 (54 pages).
U.S. Appl. No. 13/651,420 Official Action (Non-Final) dated Nov. 4, 2013 (8 pages).
U.S. Appl. No. 13/651,420 Response to Official Action (Non-Final) dated Nov. 4, 2013, submitted Nov. 21, 2013 (2 pages).
U.S. Appl. No. 13/681,440 Official Action (Non-Final) dated Oct. 24, 2013 (11 pages).
U.S. Appl. No. 13/651,420 Official Action (Non-Final) dated Jan. 6, 2014 (8 pages).
U.S. Appl. No. 13/651,420 Response to Official Action (Non-Final) dated Jan. 6, 2014, submitted Mar. 5, 2014 (9 pages).
U.S. Appl. No. 13/651,420 Official Action (Final) dated Apr. 24, 2014 (8 pages).
U.S. Appl. No. 13/651,420 Response to Official Action (Final) dated Apr. 24, 2014, submitted Jul. 22, 2014 with Request for Continued Examination (15 pages).
U.S. Appl. No. 13/651,420 Official Action (Non-Final) dated Aug. 19, 2014 (10 pages).
U.S. Appl. No. 13/651,420 Response to Official Action (Non-Final) dated Aug. 19, 2014, submitted Dec. 18, 2014 (7 pages).
U.S. Appl. No. 14/016,105 Official Action (Non-Final) dated Oct. 15, 2014 (10 pages).
U.S. Appl. No. 13/681,440 Response to Official Action (Non-Final) dated Oct. 24, 2013, submitted Jan. 20, 2014 (10 pages).
U.S. Appl. No. 13/681,440 Official Action (Final) dated Feb. 14, 2014 (14 pages).
U.S. Appl. No. 13/681,440 Response to Official Action (Final) dated Feb. 14, 2014, submitted Jul. 14, 2014 with Request for Continued Examination (14 pages).
U.S. Appl. No. 13/681,440 Official Action (Non-Final) dated Sep. 2, 2014 (19 pages).
U.S. Appl. No. 12/514,311 Official Action (Non-Final) dated Oct. 7, 2014 (11 pages).
U.S. Appl. No. 13/742,454 Response to Official Action (Non-Final) dated Oct. 7, 2013, submitted Jan. 6, 2014 (7 pages).
U.S. Appl. No. 13/742,454 Official Action (Final) dated Mar. 28, 2014 (14 pages).
U.S. Appl. No. 13/742,454 Response to Official Action (Final) dated Mar. 28, 2014, submitted Jun. 29, 2014 with Request for Continued Examination (10 pages).
U.S. Appl. No. 13/742,454 Notice of Allowance issued Aug. 21, 2014 (10 pages).
U.S. Appl. No. 13/640,519 Official Action (Non-Final) dated Dec. 24, 2013 (7 pages).
U.S. Appl. No. 13/640,519 Response to Official Action (Non-Final) dated Dec. 24, 2013, submitted Jan. 16, 2014 (2 pages).
U.S. Appl. No. 13/640,519 Official Action (Non-Final) dated Mar. 20, 2014 (15 pages).
U.S. Appl. No. 13/640,519 Response to Official Action (Non-Final) dated Mar. 20, 2014, submitted Jun. 17, 2014 (14 pages).
U.S. Appl. No. 13/640,519 Official Action (Final) dated Oct. 1, 2014 (11 pages).
U.S. Appl. No. 13/924,572 Official Action (Non-Final) dated Dec. 2, 2014 (13 pages).
European Application No. 11768544.6 Supplementary Partial European Search Report dated Nov. 13, 2014 (7 pages).
European Application No. 12734200.4 Supplementary European Search Report dated Aug. 18, 2014 (6 pages).

(56) References Cited

OTHER PUBLICATIONS

European Application No. 05810500.8 Official Action dated Nov. 3, 2014 (5 pages).
European Application No. 05810500.8 Response to Official Action dated Nov. 3, 2014, submitted Mar. 9, 2015 (31 pages).
Indian Patent Application No. 2344KOLNP2007 Office Action dated Dec. 31, 2014 (2 pages).
Indian Patent Application No. 2344KOLNP2007 Response to Office Action dated Dec. 31, 2014, submitted Aug. 7, 2015 (19 pages).
U.S. Appl. No. 14/181,673 Official Action (Non-Final) dated Jun. 3, 2015 (12 pages).
U.S. Appl. No. 13/651,420 Official Action (Final) dated Mar. 16, 2015 (6 pages).
U.S. Appl. No. 13/651,420 Response to Official Action (Final) dated Mar. 16, 2015, submitted May 14, 2015 (5 pages).
U.S. Appl. No. 13/651,420 Official Action (Final) dated Jun. 9, 2015 (9 pages).
U.S. Appl. No. 14/016,105 Response to Official Action (Non-Final) dated Oct. 15, 2014, submitted Jan. 14, 2015 (7 pages).
U.S. Appl. No. 14/016,105 Notice of Allowance dated Feb. 17, 2015 (14 pages).
U.S. Appl. No. 13/681,440 Response to Official Action (Non-Final) dated Sep. 2, 2014, submitted Feb. 25, 2015 (12 pages).
U.S. Appl. No. 13/681,440 Official Action (Final) dated Apr. 24, 2015 (21 pages).
U.S. Appl. No. 12/514,311 Response to Official Action (Non-Final) dated Oct. 7, 2014, submitted Jan. 7, 2015 (5 pages).
U.S. Appl. No. 12/514,311 Official Action (Final) dated Apr. 20, 2015 (12 pages).
U.S. Appl. No. 12/514,311 Response to Official Action (Final) dated Apr. 20, 2015, submitted Jun. 21, 2015 (10 pages).
U.S. Appl. No. 12/514,311 Official Action (Advisory Action) dated Jul. 1, 2015 (8 pages).
U.S. Appl. No. 12/514,311 Response to Official Action (Advisory Action) dated Jul. 1, 2015, submitted Jul. 20, 2015 (8 pages).
U.S. Appl. No. 12/514,311 Official Action (Advisory Action) dated Aug. 5, 2015 (6 pages).
European Application No. 10192477.7 Official Action dated Jul. 6, 2015 (5 pages).
European Application No. 11768544.6 Response to Official Action dated Dec. 2, 2014, submitted May 29, 2015 (12 pages).
U.S. Appl. No. 13/640,519 Response to Official Action (Final) dated Oct. 1, 2014, submitted Dec. 28, 2014 (15 pages).
U.S. Appl. No. 13/640,519 Official Action (Non-Final) dated May 6, 2015 (13 pages).
European Application No. 12734200.4 Response to Official Communication dated Sep. 4, 2014, submitted Mar. 4, 2015 (16 pages).
U.S. Appl. No. 13/978,538 Official Action (Non-Final) dated Jan. 23, 2015 (24 pages).
U.S. Appl. No. 13/978,538 Response to Official Action (Non-Final) dated Jan. 23, 2015, submitted May 21, 2015 (13 pages).
U.S. Appl. No. 13/978,538 Official Action (Non-Final) dated Jul. 24, 2015 (16 pages).
European Application No. 12805094.5 Supplementary Partial European Search Report dated Feb. 23, 2015 (8 pages).
European Application No. 12805094.5 Response to Supplementary Partial European Search Report submitted Apr. 2, 2015 (1 page).
European Application No. 12805094.5 Supplementary European Search Report dated Jun. 30, 2015 (14 pages).
U.S. Appl. No. 13/924,572 Response to Official Action (Non-Final) dated Dec. 2, 2014, submitted Mar. 26, 2015 (11 pages).
U.S. Appl. No. 13/924,572 Official Action (Non-Final) dated May 14, 2015 (12 pages).
PCT Appl. No. PCT/IB14/62106 International Search Report and Written Opinion dated Feb. 24, 2015 (8 pages).
PCT Appl. No. PCT/IB15/50873 International Search Report and Written Opinion dated Jun. 25, 2015 (8 pages).

US 9,657,902 B2

PERISTALTIC INFUSION PUMP WITH LOCKING MECHANISM

CROSS-REFERENCE TO RELATED APPLICATIONS

This application is a continuation-in-part of U.S. patent application Ser. No. 11/791,599, filed May 24, 2007, in the national phase of PCT/IL2005/001249, filed Nov. 24, 2005, and of PCT Patent Application PCT/IL2007/001399, filed Nov. 13, 2007. The disclosures of all of these related applications are incorporated herein by reference.

FIELD OF THE INVENTION

The present invention relates generally to medical devices, and specifically to infusion pumps.

BACKGROUND OF THE INVENTION

Various types of medical infusion pumps are known in the art. One common type of infusion pump is a peristaltic pump, in which fluid is made to flow through an elastic tube by external compression of the tube. Typically, a peristaltic mechanism, such as a set of cams or fingers, compresses the tube in a cyclic pattern at a sequence of locations along the length of the tube, so as to cause the fluid to flow through the tube at a desired volumetric rate. Peristaltic infusion pumps are described, for example, in U.S. Pat. Nos. 5,290,158, 5,395,320, and 5,807,322, whose disclosures are incorporated herein by reference, as well as in the above-mentioned PCT patent applications.

SUMMARY OF THE INVENTION

One advantage of peristaltic pumps in medical applications is that the pump mechanism is external to the flexible tube containing the fluid, thus preserving the sterility of the fluid flowing through the tube. The tube is typically part of a disposable infusion kit, while the pump itself (which may include the complete pumping mechanism, as well as a pressure sensor module) is reused many times. Embodiments of the present invention that are described hereinbelow provide devices and methods that simplify the task of attaching the infusion tube to the pump prior to use, while ensuring a secure, reliable mechanical connection between the pump mechanism and the tube.

There is therefore provided, in accordance with an embodiment of the present invention, a medical apparatus, including an infusion pump, which includes a pump body and a peristaltic mechanism, which protrudes from the pump body and is configured to exert a force on a flexible infusion tube so as to propel a fluid through the tube. A hinge receptacle is fixed to the pump body and defines a hinge axis, and a catch receptacle is also fixed to the pump body. A mechanical interface unit is configured to hold a portion of the tube, and includes a hinge insert, which is configured to engage the hinge receptacle. A catch insert is configured to lock onto the catch receptacle upon rotation of the mechanical interface unit about the hinge axis while the hinge insert engages the hinge receptacle, so as to bring the tube into engagement with the peristaltic mechanism.

In a disclosed embodiment, the peristaltic mechanism includes multiple fingers, which are driven to compress and release the tube in a predetermined cyclic pattern.

In some embodiments, the peristaltic mechanism has a linear configuration, and the mechanical interface has an elongated shape corresponding to the linear configuration of the peristaltic mechanism.

In one embodiment, the hinge receptacle includes an axle, and the hinge insert includes a saddle, which fits over the axle. The axle and saddle may be split so as to define a channel for receiving the portion of the tube. Additionally or alternatively, the catch insert includes a tooth, and the catch receptacle includes an elastic catch.

In some embodiments, the pump body includes a rim surrounding the peristaltic mechanism, and the mechanical interface unit includes collars, which are fixed to opposing ends of the portion of the tube and lodge against the rim. The infusion pump may include a door, which closes over the rim so as to enclose the peristaltic mechanism. The rim may have openings shaped to receive the tube so that the tube extends through the openings when the door is closed. Typically, the collars are configured to lodge inside the rim and have respective diameters that are larger than the openings so as to prevent axial motion of the tube after the door has been closed.

In a disclosed embodiment, the mechanical interface unit includes an anti-free-flow mechanism, which is configured to prevent flow of the fluid through the portion of the tube until the tube has been brought into the engagement with the peristaltic mechanism. Typically, the anti-free-flow mechanism can be opened manually prior to the engagement of the tube with the peristaltic mechanism, and the infusion pump includes a key, which is fixed to the pump body and is configured to release the anti-free-flow mechanism so as to prevent the flow of the fluid through the portion of the tube when mechanical interface unit is disengaged from the pump.

There is also provided, in accordance with an embodiment of the present invention, a medical device, including an interface unit body, which is configured to hold a portion of a flexible infusion tube. A hinge insert is fixed to the interface unit body and is configured to engage a hinge receptacle, which defines a hinge axis, on an infusion pump. A catch insert is fixed to the interface unit body and is configured to lock onto a catch receptacle on the infusion pump upon rotation of the mechanical interface unit about the hinge axis while the hinge insert engages the hinge receptacle, so as to bring the tube into engagement with a peristaltic mechanism of the infusion pump in order to enable the peristaltic mechanism to propel a fluid through the tube.

In a disclosed embodiment, the device includes collars, which are fixed to opposing ends of the portion of the tube and are configured to lodge against a rim surrounding the peristaltic mechanism on the infusion pump. The collars may include connectors, which connect the portion of the flexible infusion tube in the housing to upstream and downstream tube segments.

There is additionally provided, in accordance with an embodiment of the present invention, a method for infusion, including providing a mechanical interface unit, which holds a portion of a flexible infusion tube and includes a hinge insert and a catch insert. The hinge insert in inserted into a hinge receptacle, which defines a hinge axis, on an infusion pump. The mechanical interface unit is rotated about the hinge axis while the hinge insert engages the hinge receptacle, so as to bring the tube into engagement with a peristaltic mechanism of the infusion pump. The infusion pump is actuated while the tube is in engagement with the peristaltic mechanism so as to propel a fluid through the tube.

The housing of the invention preferably includes an antifree-flow mechanism to prevent the flow of fluid in the segment of the conduit in the housing when the conduit is not adjacent to the fingers. The antifree-flow has a non-obstructing position in which the antifree-flow device does not prevent flow in the conduit, and an obstructing position in which the antifree-flow device prevents flow in the conduit. The antifree-flow device is spring biased in the obstructing position, so that when the housing is swung away or detached from the body of the pump, the antifree-flow device spontaneously assumes its obstructing position. This prevents unintentional flow in the conduit when the housing is swung out or detached from the body of the pump. The antifree-flow device preferably includes an override mechanism that allows the antifree-flow device to be temporarily latched in its non-obstructing position when the housing is swung away or detached from the body in order to allow a segment of conduit to be introduced into the housing. As the housing is brought to its position in which it is attached to the pump, the antifree-flow device is brought to its unlatched non-obstructing position, regardless of whether it was previously in its obstructing position or its latched non-obstructing position. The antifree flow device may prevent flow in the conduit in both directions or only in one direction.

The present invention will be more fully understood from the following detailed description of the embodiments thereof, taken together with the drawings in which:

DETAILED DESCRIPTION OF EMBODIMENTS

Figure 1:
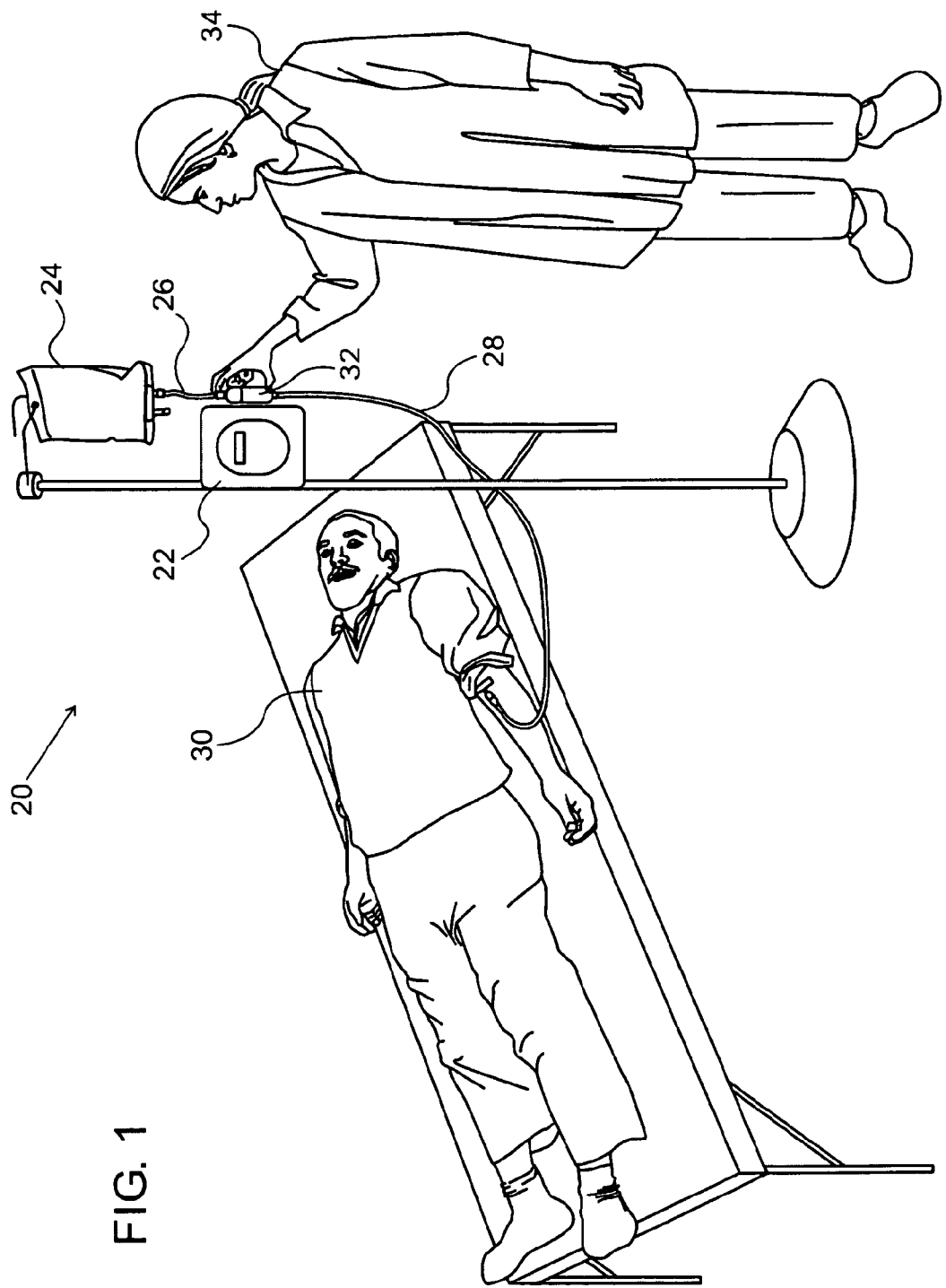
FIG. 1 is a schematic, pictorial illustration of a medical infusion system, in accordance with an embodiment of the present invention.

FIG. 1 is a schematic, pictorial illustration of a medical infusion system 20, in accordance with an embodiment of the present invention. System 20 comprises a peristaltic infusion pump 22, which pumps an infusion fluid from a reservoir 24, through an upstream tube segment 26 (commonly referred to as the "supply line") and a downstream tube segment 28 (commonly referred to as the "patient line"), into a vein of a patient 30. This particular type of infusion system is shown here by way of illustration, but the principles of the present invention, as described hereinbelow, may likewise be applied to other types of peristaltic pumps and in substantially any sort of application that uses such pumps, such as delivery of drugs and of both enteral and parenteral nutrition. Although the pictured embodiment represents a clinical environment, the devices and methods described herein are also suitable for ambulatory and home use, particularly since they can operate even when the pump and reservoir are at the same level as or lower than the patient.

Tube segments 26 and 28 are connected to a mechanical interface unit 32, which couples to pump 32 in a manner that is shown and explained below in greater detail. Unit 32 contains a tube portion (not shown in FIG. 1) that is connected in series with tube segments 26 and 28, thus defining a flow path from reservoir 24 to patient 30. In a typical implementation, tube segments 26 and 28 comprise polyvinyl chloride (PVC), while the portion of the tube in unit 32 comprises silicone rubber. Tube segments 26 and 28 and the portion of the tube in unit 32 may thus be regarded as a single tube. Alternatively, the tube segments and the portion of the tube in unit 32 may be fabricated as a unitary element from silicone or from another material with similar properties. The term "tube," in the context of the present patent application and in the claims, should thus be understood as referring both to unitary tubes and to any arrangement of tube segments and portions in series that defines a tube-like flow path.

As shown in detail in the figures that follow, mechanical interface unit 32 couples with pump 22 so as to bring the tube into engagement with the peristaltic mechanism of the pump. Typically, unit 32 is supplied as a pre-assembled, disposable kit, along with tube segments 26 and 28. Unit 32 is constructed so as to enable an operator 34 to connect the unit to pump 22 stably and reliably by fitting the unit against the pump and snapping it into place with only light pressure. Because the connection between unit 32 and pump 22 is self-aligning, operators are able to perform this operation with a single hand, after only minimal training. After use, unit 32 may be snapped off pump 22 and discarded together with the tube.

Figure 2:
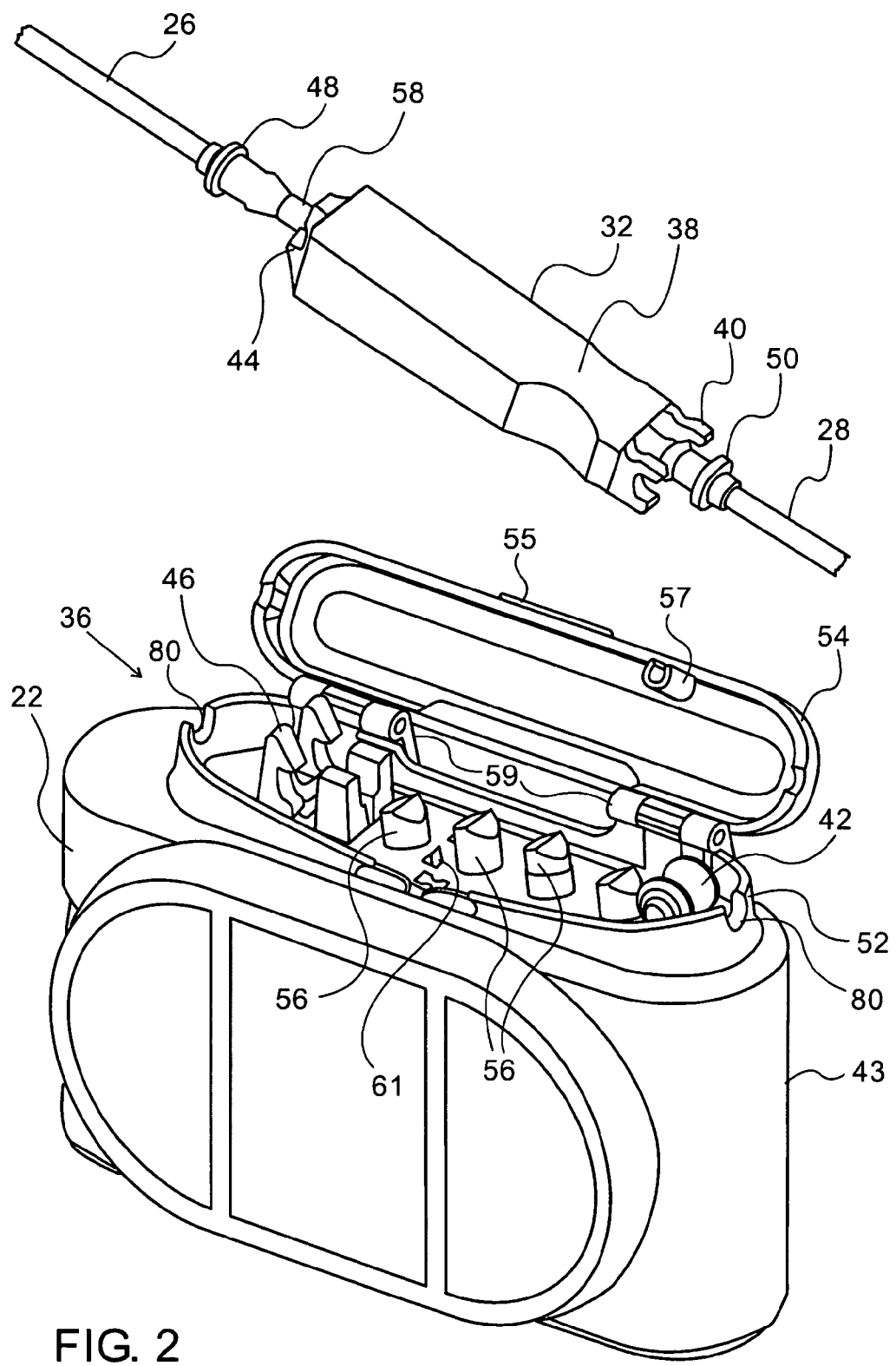
FIG. 2 is a schematic, pictorial illustration showing coupling of a mechanical interface unit with an infusion tube to an infusion pump, in accordance with an embodiment of the present invention.
Figure 3:
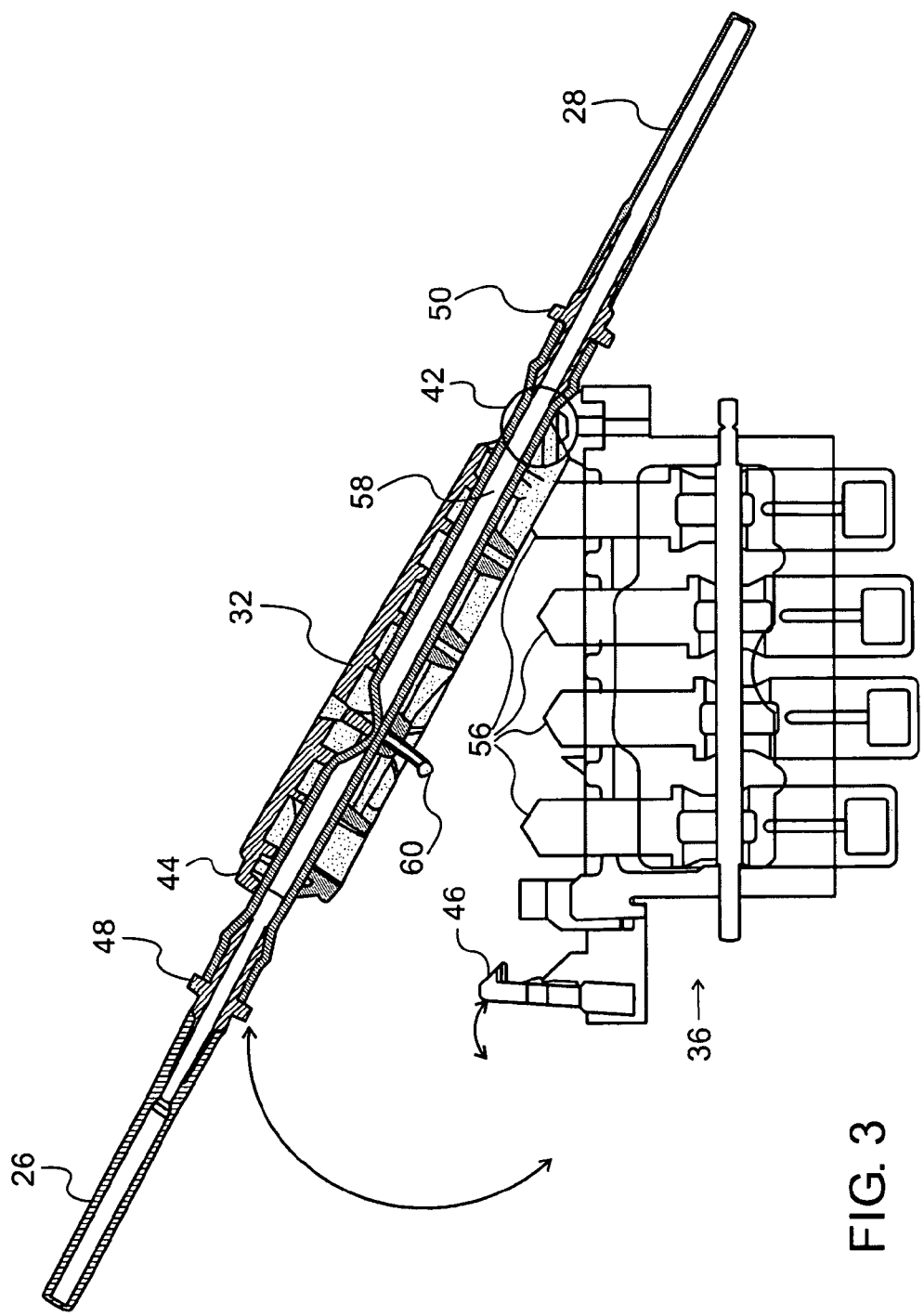
FIG. 3 is a schematic, sectional illustration of a part of an infusion pump and a mechanical interface unit during coupling of the mechanical interface unit to the infusion pump, in accordance with an embodiment of the present invention.

Reference is now made to FIGS. 2 and 3, which schematically show details of pump 22 and of mechanical interface unit 32 during preliminary stages of attaching the unit to the pump, in accordance with an embodiment of the present invention. FIG. 2 is a pictorial view, while FIG. 3 shows details of the mechanical interface unit and of a peristaltic mechanism 36 of the pump in sectional view.

Mechanical interface unit 32 comprises a body 38, which hold a portion 58 of the flexible infusion tube. In the embodiment shown in the figures, portion 58 of the tube is connected to segments 26 and 28 by connectors 48 and 50, respectively. Body 38 has an elongated shape, corresponding to the linear configuration of mechanism 36. Mechanism 36 comprises multiple fingers 56, which move up and down to compress and release tube portion 58 in a predetermined cyclic pattern, so as to propel fluid downstream from tube segment 26 to tube segment 28. Details of the operation of this sort of multi-finger peristaltic mechanism are described in the above-mentioned U.S. patent application Ser. No. 11/791,599 and in PCT Patent Applications PCT/IL2007/001398 and PCT/IL2007/001400, filed Nov. 13, 2007, whose disclosures are incorporated herein by reference.

Unit 32 comprises a hinge insert 40 at one end of body 38 (in this case, the downstream end) and a catch insert 44 at the other (upstream) end. To assemble unit 32 onto pump 22, the operator first brings hinge insert 40 into engagement with a hinge receptacle 42 on a body 43 of the pump. In this position, unit 32 is aligned in a plane of peristaltic mechanism 36 (i.e., the plane of the page in FIG. 3), but is able to rotate within the plane about an axis defined by the hinge receptacle. The operator rotates unit 32 about this axis, while the hinge insert engages the hinge receptacle, until catch insert 44 engages and locks onto a catch receptacle 46 on the pump body. The catch receptacle is spring-loaded (or otherwise elastic) so that it slides over and then locks onto the catch insert as the operator presses unit 32 down against pump 22. Once engaged and locked in this manner, movement of unit 32 is restricted in all directions. Unit 32 may subsequently be released from pump 22 simply by opening the catch and rotating the unit away from the pump.

The rotational mode of assembly described above is advantageous in that it ensures accurate alignment of tube portion 58 with mechanism 36, even in one-handed operation. Consequently, good flow accuracy is achieved without the need for very careful insertion of the tube into the pump. The inventors have found that the combination of this sort of mechanical interface unit with the type of peristaltic pump described in the above-mentioned patent applications gives better than 2.5% accuracy in flow control over long periods of time.

The position of hinge receptacle 42 may be pre-adjusted so that interface unit 32, when engaged and locked onto pump 22, is properly located relative to fingers 56. For example, the hinge receptacle may be connected to pump body 43 by a single screw (not shown), which permits the receptacle to be moved and then tightened in place in a factory calibration procedure. Because the hinge receptacle is located on the downstream side of mechanism 36, this sort of calibration can be used to find the optimal balance between pressure buildup and energy consumption for propelling fluid at high pressure.

Furthermore, this mode of assembly gives the operator a mechanical advantage in closing the catch insert against the catch receptacle, so that relatively little force is needed to make a secure connection. In a clinical version of system 20, the inventor has found that less than 2 kg of force, typically about 1.2 kg, is sufficient for this purpose.

Another advantage of mechanical interface unit 32 and the mating structure on pump 22 is that they ensure that the tube will be assembled onto the pump in the proper direction: Because one type of mating connector is used at the upstream end of unit 32, and a different type of mating connector is used at the downstream end, it is impossible for the operator to accidentally attach the tube in the reverse direction.

In the embodiment pictured in the figures, hinge receptacle 42 has the form of a split axle, while hinge insert 40 has the form of a split saddle. At the other end of unit 32, catch insert 44 has the form of a split tooth, while catch receptacle 46 comprises a dual, concave catch. Tube portion 58 thus passes through the opening between the sides of insert 40, receptacle 42, insert 44 and receptacle 46. This particular configuration of the hinge and catch parts of pump 22 and unit 32 has been found to provide mechanical stability, durability and ease of assembly.

On the other hand, other configurations of the hinge and catch parts are also possible, as will be apparent to those skilled in the art, and are considered to be within the scope of the present invention. For example, the "male" and "female" elements on the interface unit and pump body may be reversed, so that the hinge and catch inserts on the interface unit have the form of an axle and elastic catch, while the hinge and catch receptacles on the pump have the form of a saddle and tooth. Other suitable hinge and catch arrangements are described in the above-mentioned U.S. patent application Ser. No. 11/791,599.

After assembly of interface unit 32 onto pump 22, a cover 54 may be closed against a rim 52 over the unit for added security. A locking mechanism 55 on the cover prevents accidental opening. Pump 22 may comprise a sensor (not shown) for detecting whether cover 54 is closed, such as a magnetic sensor, which detects the proximity of a magnet 57 attached to the cover. Until the operator is ready to close the cover, however, spring-loaded hinges 59 hold the cover open so that it does not interfere with handling of the interface unit.

Interface unit 32 also comprises an anti-free-flow mechanism 60, which closes off tube portion 58 until the interface unit has been securely connected to pump 22, in order to prevent uncontrolled flow of infusion fluid into the patient's body. Mechanism 60 may be opened manually if necessary, and opens automatically when the interface unit is mounted on the pump. A key 61 on the pump body (FIG. 2) releases mechanism 60 if the mechanism was opened manually before mounting interface unit 32 on the pump, so as to ensure that the mechanism closes (and prevents inadvertent free flow) when the interface unit is disengaged from the pump. Details of this sort of anti-free-flow mechanism mechanism are described in the above-mentioned U.S. patent application Ser. No. 11/791,599 and in PCT Patent Application PCT/IL2007/001405, filed Nov. 13, 2007, whose disclosure is incorporated herein by reference.

Figure 4:
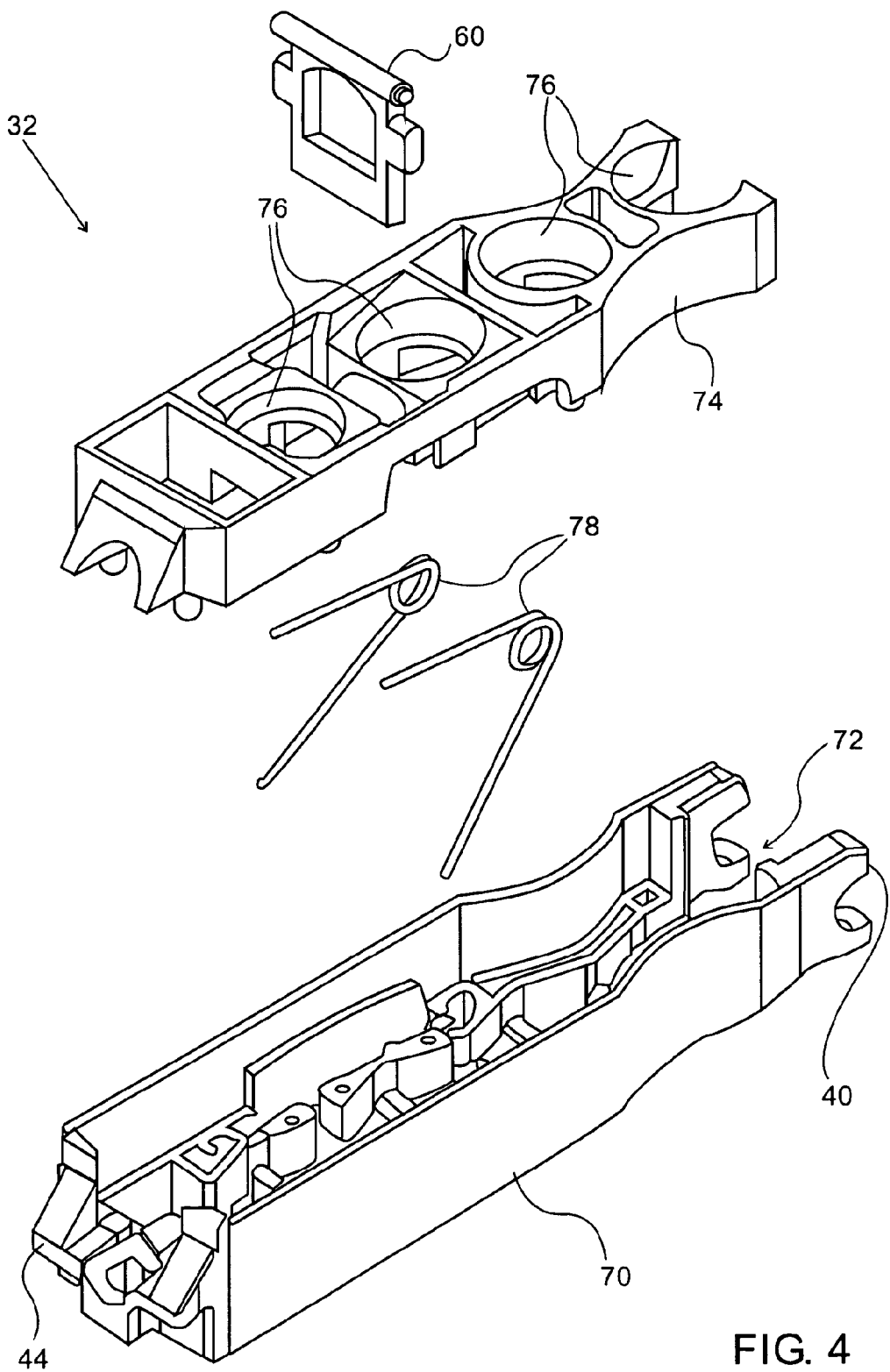
FIG. 4 is a schematic, exploded view of a mechanical interface unit, in accordance with an embodiment of the present invention.

FIG. 4 is a schematic, exploded view of interface unit 32, in accordance with an embodiment of the present invention. Unit 32 comprises an outer shell 70 and an inner shell 74, which define a central channel 72 for receiving tube portion 58. To assemble unit 32, tube portion 58 is placed in channel 72, and shells 70 and 74 are then fitted together, thus holding the tube portion securely in place. Anti-free-flow mechanism 60 is mounted in a slot in unit 32 against springs 78, which hold the mechanism in its closed position. (Alternatively, a single spring may be used for this purpose.) Shell 74 contains finger holes 76, through which fingers 56 protrude in order to engage and compress the tube portion inside.

Figure 5:
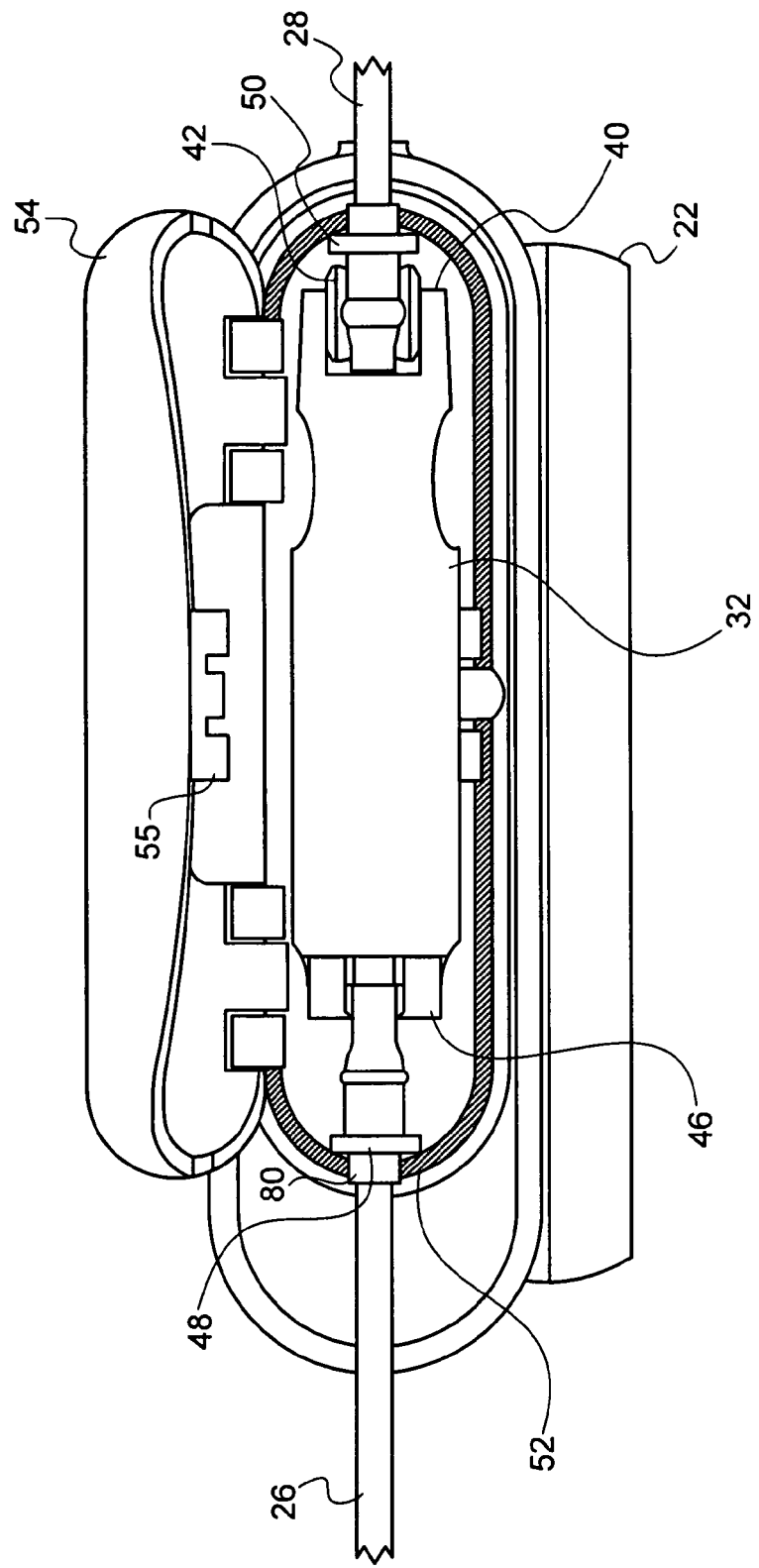
FIG. 5 is a schematic side view of an infusion pump to which a mechanical interface unit with an infusion tube has been coupled, in accordance with an embodiment of the present invention.
Figure 6:
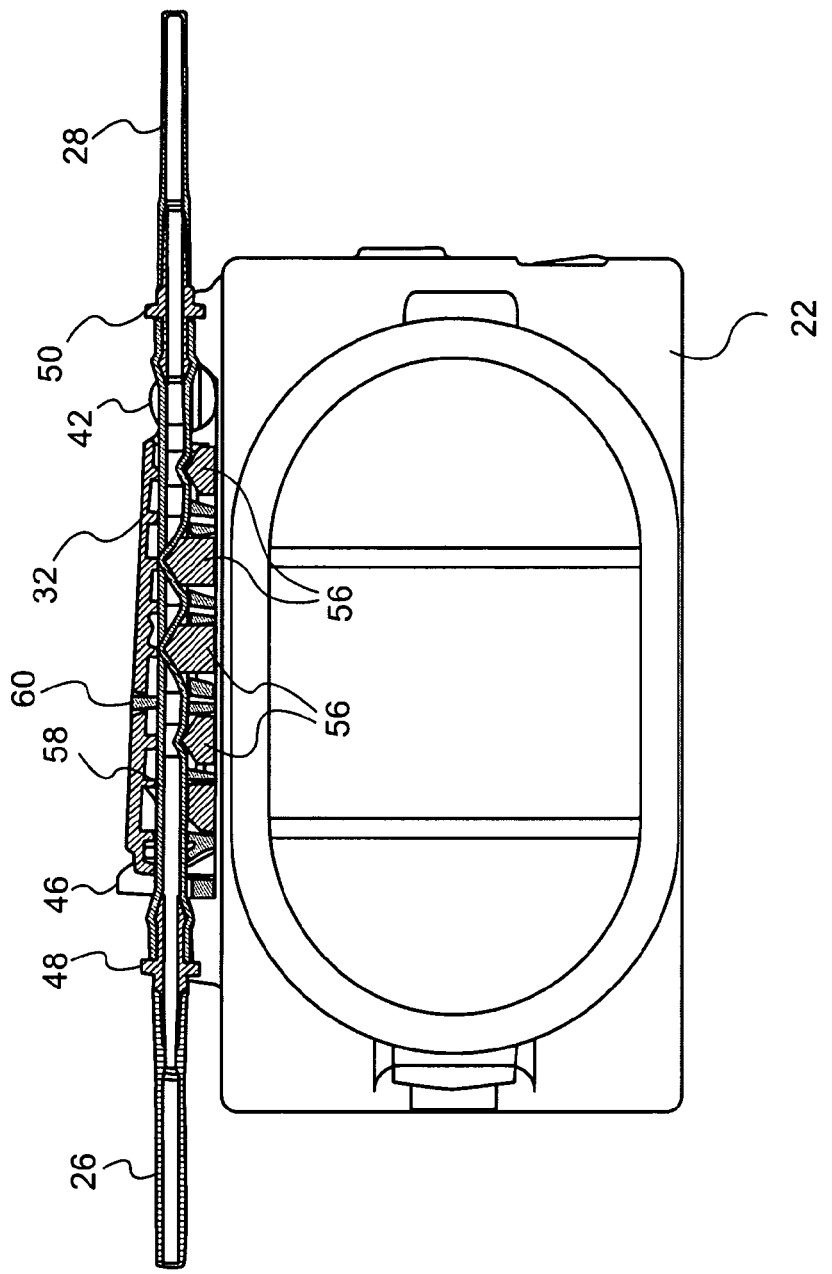
FIG. 6 is a schematic, frontal, partially sectional view of an infusion pump to which a mechanical interface unit with an infusion tube has been coupled, in accordance with an embodiment of the present invention.

Reference is now made to FIGS. 5 and 6, which show interface unit 32 assembled onto pump 22, in accordance with an embodiment of the present invention. FIG. 5 is a side view, while FIG. 6 is a frontal, partly sectional view. In these figures, catch receptacle 46 has closed over catch insert 44, thus bringing tube portion 58 into engagement with peristaltic mechanism 36 of pump 22. The peristaltic mechanism is thus able to propel the infusion fluid through the tube. Tube segments 26 and 28 protrude through holes 80 in rim 52, which are similar in shape and diameter to the tube segments. Collars on connectors 48 and 50, which have a larger diameter than the holes, lodge against the inner side of rim 52, thus enhancing the stability and security of unit 32, particularly against pulling forces that may be exerted on tubes 26 and 28. Anti-free-flow mechanism 60 is held open. Fingers 56 alternately compress and release tube portion in the appropriate pattern, at a frequency chosen to give the desired volumetric flow of fluid through the tube.

Although the embodiment shown in the figures uses a particular type of linear finger-based mechanism, the principles of the present invention may similarly be applied to peristaltic pumps using other types of mechanisms, including cam-based mechanisms, as well as circular mechanisms. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An interface unit body configured to be engaged to an infusion pump wherein the infusion pump includes a key, the interface unit body comprising:
   a housing to receive a tube; and
   an anti-free flow mechanism including at least three mechanical states:
   (1) a safety default closed state to prevent flow of fluid through the tube when disengaged from the infusion pump,
   (2) a mechanically latched open state to override the safety default closed state when disengaged from the infusion pump, and
   (3) a default open state to allow controlled flow of fluid through the tube when engaged to the infusion pump, wherein said anti free flow mechanism is caused to transition to said safety default closed state upon disengagement of the interface unit body from the infusion pump by the key.

2. The interface unit body of claim 1, wherein said mechanically latched open state and said default open state are further configured to enable insertion of the tube.

3. The interface unit body of claim 1, further comprising the tube, wherein the tube is a flexible infusion tube.

4. The interface unit body of claim 1, wherein said mechanically latched open state is further configured to enable free flow of fluid through the tube.

5. The interface unit body of claim 1, wherein said interface unit body is configured to allow fluid to propel through the tube by a peristaltic mechanism associated with the infusion pump when in the default open state.

6. The interface unit body of claim 1, wherein said interface unit body is configured to allow fluid to propel through the tube by a peristaltic mechanism associated with the infusion pump when engaged in the infusion pump.

* * * * *